United States Patent [19]

Reimels et al.

[11] Patent Number: 4,705,500
[45] Date of Patent: Nov. 10, 1987

[54] OPHTHALMIC ASPIRATOR-IRRIGATOR

[75] Inventors: Harry G. Reimels, Braintree; David A. Walsh, Waltham; Michael J. Arsenault, Brant Rock, all of Mass.

[73] Assignee: Mentor O & O, Inc., Norwell, Mass.

[21] Appl. No.: 886,371

[22] Filed: Jul. 17, 1986

[51] Int. Cl.⁴ .............................................. A61B 17/32
[52] U.S. Cl. ...................................... 604/35; 604/22; 604/30
[58] Field of Search .................. 604/22, 30, 31, 32, 604/33, 34, 35, 50, 51, 155; 128/325

[56] References Cited

U.S. PATENT DOCUMENTS

| | | | |
|---|---|---|---|
| 4,184,510 | 1/1980 | Murry et al. | 604/30 |
| 4,299,221 | 11/1981 | Phillips et al. | 604/30 |
| 4,493,695 | 1/1985 | Cook | 604/30 |
| 4,516,398 | 5/1985 | Wuchinich | 604/35 X |
| 4,517,977 | 5/1985 | Frost | 604/22 X |
| 4,609,368 | 9/1980 | Dotson | 604/35 X |

Primary Examiner—Edward M. Coven
Attorney, Agent, or Firm—Morse, Altman & Dacey

[57] ABSTRACT

An ophthalmic aspirator-irrigator system for use during cataract surgery is disclosed. The system frees both hands of the surgeon for the surgical tasks and leaves the automatic operation of the system to a single control input operated by a foot pedal. The pedal controls both the aspiration and ejection functions as well as their respective speeds. The opthalmic aspirator-irrigator system essentially comprises a hand-held device, a control box operable by the foot pedal and a power cord connecting the device with the box. A source of fluid is connected via a tube to the device to effect the irrigation function. The control box includes a power source and a circuit coupled to the source and via the cord to the device. Preferably, the circuit includes a bridge output network controlled by a linear motion slide type potentiometer controlled by the foot pedal. The circuit further includes dual DC amplifiers and a pulse-width modulated gate circuit to operate the device bidirectionally with a smooth, continuous and varibale speed. The foot pedal has two zero control positions: in its off, non-depressed position and in its off position about midway through the pedal's downward travel.

18 Claims, 18 Drawing Figures

OPHTHALMIC ASPIRATOR-IRRIGATOR

BACKGROUND OF THE INVENTION

1. Field of the Invention

The present invention relates generally to ophthalmic instruments and, more particularly, to an ophthalmic aspirator-irrigator useful during extracapsular cataract surgery.

2. The Prior Art

Extracapsular cataract surgery involves the break-up and removal of the cortex of the cataract and other tissue from the eye by an aspirator instrument and the continuous substitution of fluids back into the eye to maintain appropriate internal pressure therein lest it collapses. Extracapsular cataract surgery is typically performed with small and delicate manually operated hand-held instruments viewed through a microscope. The precision and delicateness with which ophthalmic surgery is performed requires very durable precision instruments. A great variety of such precision instruments are presently in use. One such instrument employs a pulsating high velocity liquid jet to disintegrate the cortex and removing by suction the fluid entraining the disintegrated tissue. See U.S. Pat. No. 3,930,505. Another instrument uses a pair of jaws for engaging the cortex and removing portions thereof by moving the jaws relative to one another. See U.S. Pat. No. 3,996,935. A further instrument involves one blade surface rotating relative to another. See U.S. Pat. No. 4,167,943. Another instrument includes a rotating stylus, a fluid source for washing away cut tissue and a vacuum tube for removing slurry consisting of the cut tissue and washing fluid. See U.S. Pat. No. 4,320,761. A still further instrument uses a handpiece with an ultrasonic motor for driving a needle, including a cutting tube mounted within a needle, with irrigation and aspiration also provided. See U.S. Pat. No. 4,428,748. Another instrument discloses an automatically operated device, which can be held and operated in one hand by the user and which does not utilize long tubing in operation and wherein the controls are mounted on the handpiece itself. See U.S. Pat. No. 4,508,532. As observed in this Pat. No. 4,508,532, the pumps are connected to the aspiration cannula by long flexible tubing. Such connection can cause fluctuations in the aspiration pressures and time delays in the operation of the instruments.

SUMMARY OF THE INVENTION

It is a principal object of the present invention to overcome the disadvantages of prior art devices by providing an improved ophthalmic aspirator-irrigator system particularly for use during extracapsular cataract surgery.

More specifically, it is an object of the present invention to provide an ophthalmic aspirator-irrigator system particularly adapted for use during extracapsular cataract surgery and essentially comprising a hand-held device, a foot operable control box and a power cord operatively connecting the device with the control box. The hand-held device is designed to function both as an aspirator as well as an irrigator, with aspiration and ejection functions and their respective aspiration and ejection speeds controlled by a single control input. The control box is provided with a foot pedal which serves as the single control input of the ophthalmic aspirator-irrigator system. Preferably, a source of gravity-fed fluid is connected via a flexible tube to the hand-held device to effect the irrigation function. The handheld device includes a cannula formed with a hollow cone and a needle projecting therefrom, the needle having a central channel in communication with the cone at one end and terminating in an aspiration port at the other end, and an annular channel surrounding the central channel and communicating with a hollow arm provided on the cone at one end and terminating in a pair of openings at the other end; a pressure-differential creating means connected to the central channel of the cannula; drive means for bidirectionally driving the pressure-differential creating means; and a connecting member mounted adjacent the drive means and replaceably securing the cannula thereto. The control box further includes a power source, which preferably comprises a battery pack, and a circuit coupled to the source. Preferably the circuit, which includes dual D.C. amplifiers and a pulse-width modulated gate circuit, controls the drive means bidirectionally with a smooth, continuous speed control. Preferably, the system includes a linear motion slide-type potentiometer controlled by the foot pedal.

Other objects of the present invention will in part be obvious and will in part appear hereinafter.

The invention accordingly comprises the ophthalmic aspirator-irrigator of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein.

DETAILED DESCRIPTION OF THE PREFERRED EMBODIMENTS

The illustrated preferred embodiments of an ophthalmic aspirator-irrigator system constructed in accordance with the present invention have been designed for use during extracapsular cataract surgery both to remove the cortex of the cataract and to provide an infusion of replacement fluid to maintain appropriate internal pressure in the anterior segment of the eye.

Figures 1, 2:
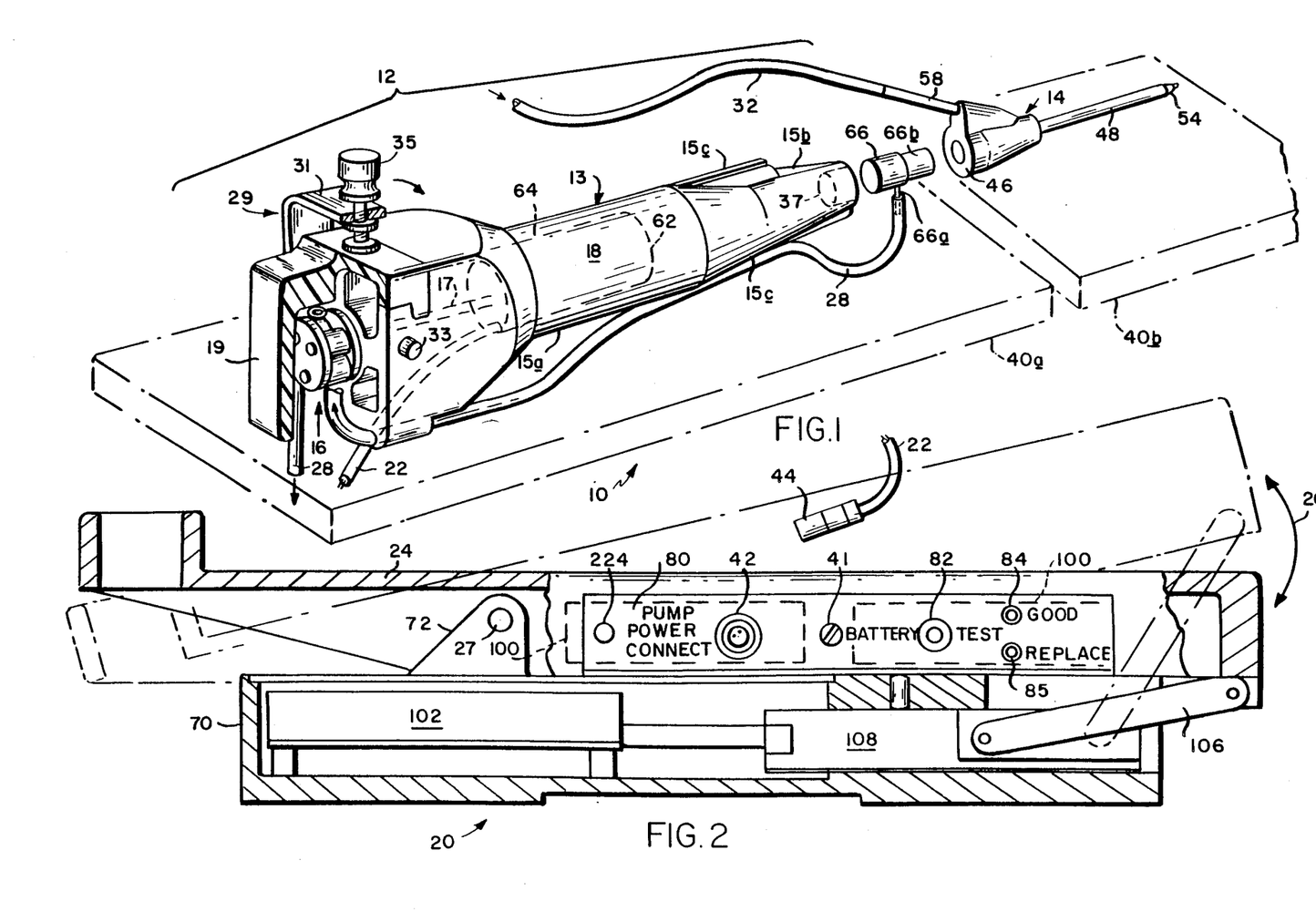
FIG. 1 is a perspective explosive view, partly in section, of an ophthalmic aspirator-irrigator instrument constructed in accordance with the present invention.
FIG. 2 is a longitudinal elevation, partly in section, of control means for operating the ophthalmic aspirator-irrigator instrument of FIG. 1.

The Embodiment of FIGS. 1 and 2

The ophthalmic aspirator-irrigator instrument 10 essentially comprises a hand-held device 12, control means 20 and a flexible power cord 22 coupling the control means 20 to the device 12. The control means 20 is portable and is provided with a foot pedal 24. The foot pedal 24 represents a single control input to the instrument 10, freeing thus both hands of the surgeon for the operative tasks in front of him. The foot pedal 24 is designed to travel through an arc 26 of displacement. The position of the pedal 24 along this arc 26 of displacement controls both the speed and the aspiration or ejection functions of the device 12, as will be more evident from below.

The hand-held device 12 includes a cannula 14, and a housing 13 including a pressure-differential creating means 16 operatively connected to the cannula 14, and drive means 18 to drive the pressure-differential creating means 16. Preferably, the pressure-differential creating means 16 comprises a peristaltic pump rotated by a shaft 17, and having a flexible tubing 28 wound about it and held in place by a tube retaining member 19. One end of the tubing 28 is connected to a connecting member 66, and the other to a collection pouch 21, note FIG. 5. Preferably, the collection pouch 21 is clamped to a surgical drape 23, by a clamp 25, near an operative site 27.

The housing 13 preferably is formed, as for instance by injection forming in a die, of a suitable hard plastic material, such as polycarbonate or the like. The housing 13 essentially is formed of a hollow main frusto-conical section 15a. The main section 15a, in addition to accommodating the drive means 18 within its hollow interior, is glued or otherwise secured to a heavier section 15b. Section 15b is designed in its rear removably to mount the tube retaining member 19 thereto, with the aid of a clamp assembly 29. Clamp assembly 29, preferably formed of a suitable metal, comprises a U-shaped clamp 31, designed to pivot about a pair of mounting pins 33 formed on the housing 13, and a fastening member 35, designed to bear down and to hold the tube retaining member 19 in place, as shown. If either the drive means 18 or the thereby driven persistaltic pump 16 needs servicing or the flexible silicone tubing 28 needs to be replaced, the fastening member 35 is loosened until the clamp 31 can be pivoted, in the direction of the arrow, out of engagement with the tube retaining member 19. Member 19 can then be removed, exposing thereby the pump 16 and the tubing 28.

The main frusto-conical section 15a is formed at its front center with an axial tubular opening 37 designed frictionally to accommodate therein the connecting member 66. Member 66 is provided with an elbow 66a and an axial passage 66b communicating therewith. The elbow 66a is designed removably to secure one end of the tubing 28 thereto. The main frusto-conical section 15a furthermore is preferably provided with a pair of longitudinal channels 15c designed respectively and removably to secure therein portions of the flexible tubings, as illustrated with reference to the tubing 28 being partially wedged in one of the channels 15c.

Figure 6:
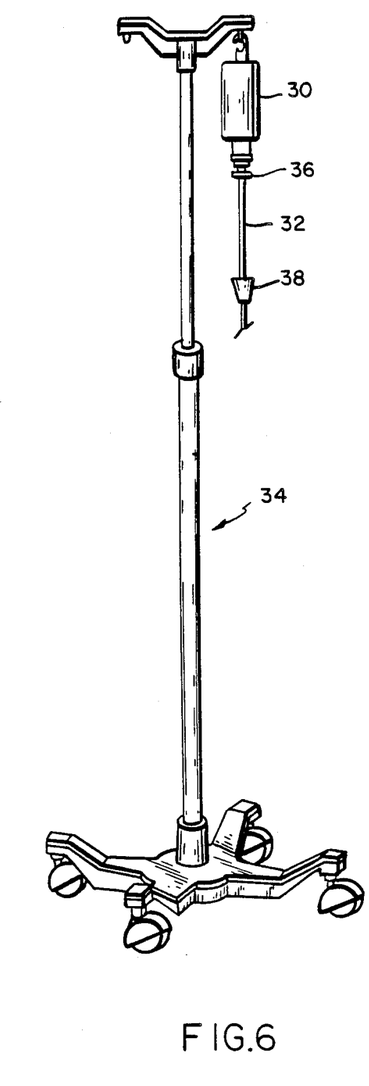
FIG. 6 is a perspective view of an adjustable stand carrying a source of fluid.
Figure 7:
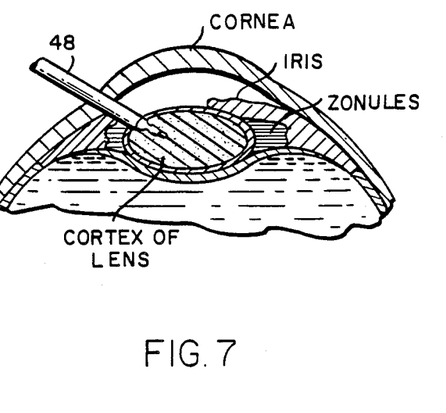
FIG. 7 is a fragmentary section of an eye and illustrates the use of the ophthalmic aspirator-irrigator instrument of FIG. 1 during cataract surgery.

A source of fluid 30, preferably an inverted plastic bottle filled with saline solution, is connected via a flexible tube 32 to the cannula 14, observe FIG. 6. The bottle 30 preferably is hung, as known, on a vertically adjustable stand 34 so as to allow for the gravity-feeding of the fluid via the cannula 14 into the eye. A clamp 36 and an appropriate filter 38 preferably are incorporated in the tube 32.

Preferably, both the cannula 14 and the housing 13 containing the pressure-differential creating means 16 are enclosed in a suitable container to maintain the same in sterile condition. The container can be a single container, formed of a semi-rigid transparent plastic material, or it can comprise two separate containers as shown: container 40a, preferably formed of a semi-rigid transparent plastic material and, container 40b, preferably formed of a flexible yet strong transparent plastic material.

Following use, the hand-held device 12, including both the cannula 14 and the thereto attached power cord 22, all of which are autoclavable, preferably are sterilized before any reuse. Sterilization may be effected in an autoclave, by gamma sterilization or by ETO. On the other hand, the flexible tubings 28 and 32, designed for single use only, together with the pouch 21, preferably are discarded after operative use and replaced with sterile tubings immediately before operative re-use of the the instrument 10.

The control box 20 is provided with a jack 42 to receive a plug 44 carried by the free end of the flexible power cord 22. It is to be noted that cord 22 is but a power cord, carrying but an electrical signal. It is not a long tubing connecting the cannula 14 to a distant pump for creating the required negative aspiration pressures, as is the case in some prior art devices, which can cause fluctuations in the aspiration pressures and delays in the use of the instrument.

Figure 8:
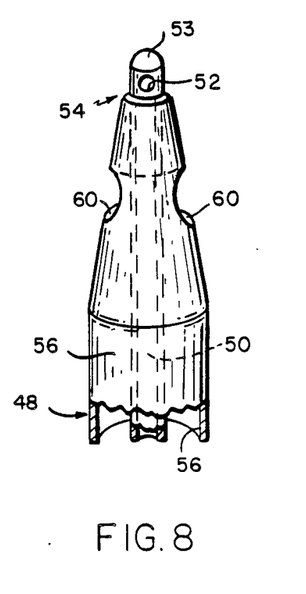
FIG. 8 is an enlarged perspective of the tip of a part of the ophthalmic aspirator-irrigator instrument of FIG. 1.
Figure 9:
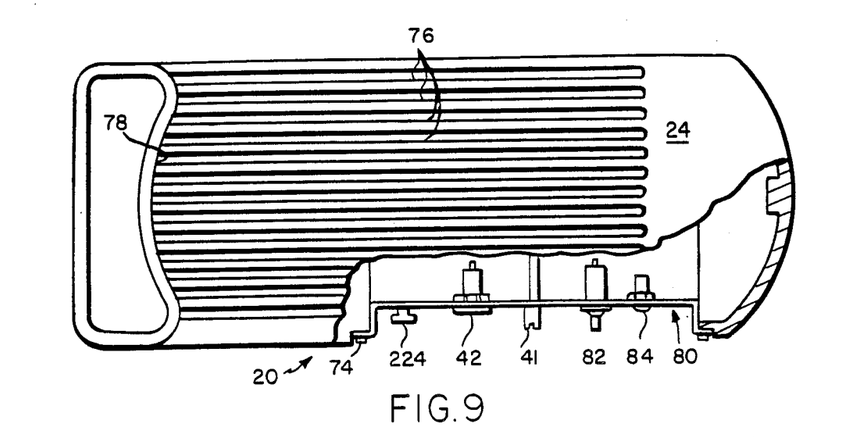
FIG. 9 is a plan view, partly in section, of the control means of FIG. 2.

The cannula 14 essentially comprises two parts: a hollow cone 46 and a needle 48 concentrically extending therefrom. The needle 48 is formed with a central channel 50, which is in fluid communication with the hollow cone 46 at one end and terminates in an aspiration port 52 and a rounded end 53 near a tapered portion 54 of the needle 48, note FIGS. 1 and 8. An annular channel 56 surrounds the central channel 50 and is in fluid communication with a hollow arm 58 at one end, and terminating in a pair of irrigation channels 60, also in the tapered portion 54 of the needle 48 but offset from the aspiration port 52 and at right angles thereto, as may be best observed in FIG. 8. The hollow arm 58 preferably is formed integral with the hollow cone 46 of the cannula 14. The cannula 14 can be formed of a suitable metal, such as stainless steel, or it may be formed as by injection forming or compression molding of a suitable plastic material, such as polypropylene, in a suitable mold (not shown) in which the needle 48 had been inserted previously. The needle 48, however, preferably is made of metal, such as stainless steel. The hollow cone 46 of the cannula 14 is, of course, designed to fit snugly about the front frusto-conical end of the connecting member 66.

The pressure-differential creating means 16, whose function is to create a pressure-differential within the central channel 50 of the cannula 14, preferably comprises a persistaltic pump. The pressure-differential created by the pump 16 is with respect to ambient, and can be either a positive or a negative pressure emanating from the aspiration port 52, depending on how it is driven by the drive means 18.

With the hollow cone 46 of the cannula 14 in place over the frusto-conical shaped end of the connecting member 66, the central channel 50 of the cannula 14 is in fluid-communication with the flexible tubing 28. Rotation of the drive shaft 17 and thereby of the peristaltic pump 16 clockwise creates a positive pressure within the central channel 50 of the cannula 14, causing whatever may be within the channel 50 or the aspiration port 52 (be it air, liquid or slurry) to be ejected therefrom via the aspiration port 52. Conversely, rotation of the shaft 17 and of the pump 16 counter-clockwise creates a negative pressure within the central channel 50 of the cannula 14, causing the cannula 14 to aspirate via the aspiration port 52 whatever may be in the vicinity of the aspiration port 52. The drive means 18 for driving the pressure-differential creating means 16 essentially comprises a DC micro-motor 62, a gear head 64, and the drive shaft 17.

The foot-operable control unit 20, as illustrated in FIGS. 2, 9, 10 and 11, in addition to the pedal 24, further is provided with a power source 100, preferably comprising a six volt DC battery pack, and a control circuitry 102 connected to the power source 100 and to the jack 42. The unit 20 also can be operated via a 110 VAC power source, with the aid of a transformer and rectifier, not shown. Control of the circuitry 102 is effected via a potentiometer 104. The potentiometer's 104 electrical position, hence its wiper voltage, is controlled by and is linearly proportional to the position of the pedal 24 along its arc of displacement 26 about a fulcrum 27. The pedal's 24 position along the arc of displacement 26 is transmitted to the potentiometer 104 via a link 106 and a sliding member 108.

Figure 10:
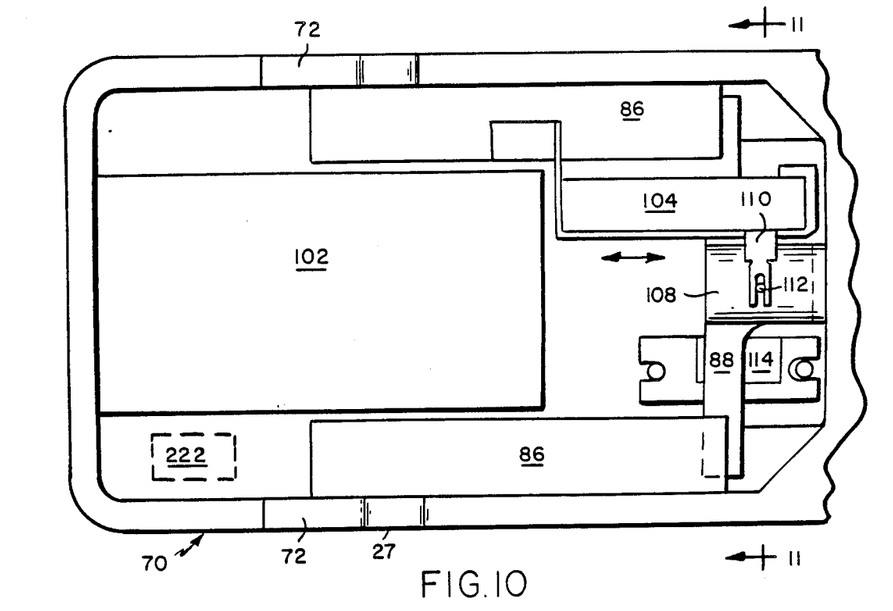
FIG. 10 is a fragmentary plan view, on an enlarged scale, of the control means of FIGS. 2.
Figure 11:
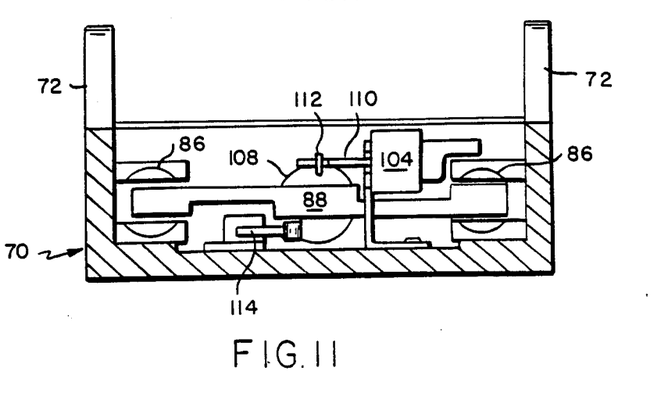
FIG. 11 is an elevation, partly in section, along the line 11—11 of FIG. 10.
Figure 17:
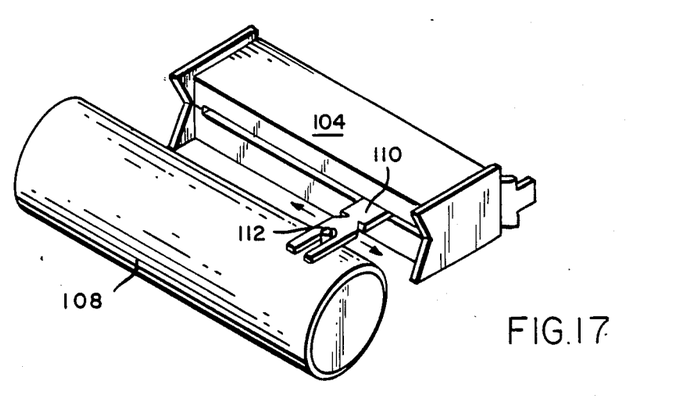
FIG. 17 is a perspective view, on an enlarged scale, of an operative part of the control means shown in FIGS. 2, 10 and 11.

The potentiometer 104 may be of the conventional type. Preferably however, it comprises a linear motion slide-type potentiometer as best illustrated in FIGS. 10 and 17. The liner motion slide-type potentiometer 104 is provided with a slidable actuating arm 110, designed to be axially displaced substantially along the axial length of the potentiometer 104. The actuating arm 110 is, in turn, caused to be axially displaced by a drive pin 112, secured to the sliding member 108.

The foot-operable control unit 20 essentially comprises the foot pedal 24 and a control box 70 provided with a pair of ears 72 whose bores serve as the fulcrum 27 for the foot pedal 24. The foot pedal 24 in turn is formed with a pair of pins 74 rotatably mounted within the bores. The underside of the control box 70 preferably is provided with a non-skid surface and/or a plastic or rubber mat. Preferably, both the foot pedal 24 and the control box 70 are formed of a suitable light metal, such as aluminum. Preferably, the upper surface of the foot pedal 24 is provided with a plurality of parallel ribs 76 running lengthwise thereof, and with a semi-circular heel rest 78. Preferably, on an indented side surface plate 80 of the foot pedal 24, observe FIGS. 2 and 9, there is provided a knob 82 and a pair of L.E.D.'s 84 and 85, in addition to the pump power connect jack 42. Manual depression of the knob 82 will cause one of the L.E.D.'s 84 or 85 to light up, indicating whether the batteries 100 are in good working order or need to be replaced. The plate 80 is removably secured to the side of the foot pedal 24 by a screw 41.

Axial motion and control of the actuating sliding member 108 within the control box 70 is facilitated by a pair of spring mounts 86 mounted astride a control circuitry 102, observe FIG. 10. The pair of spring mounts 86 are operatively connected to the actuating sliding member 108 by a bar member 88, observe FIGS. 10 and 11. Axial displacement of the sliding member 108 from a position of rest to its position, as illustrated in FIG. 10, against the force of the spring mounts 86, causes the corresponding axial displacement of the actuating arm 110 of the sliding potentiometer 104. The initial axial displacement of the actuating arm 110 also triggers a micro-switch 114, causing battery power to be applied via the power cord 22 to the drive means 18.

Figure 12:
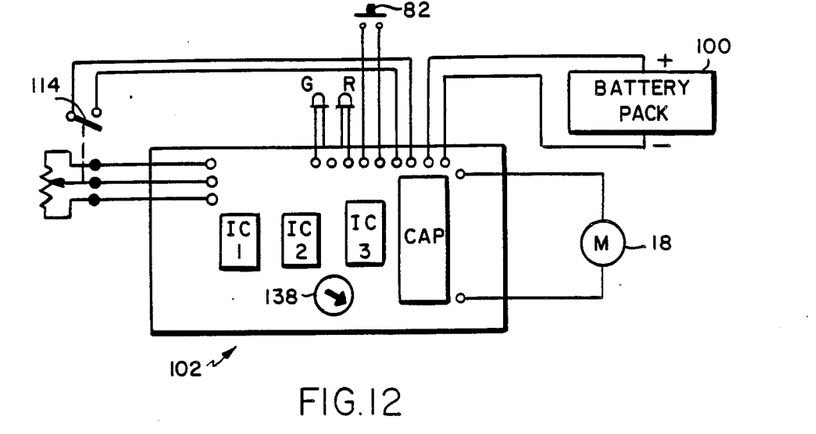
FIG. 12 is a block diagram of a control circuit for the operation of the ophthalmic aspirator-irrigator instrument according to the invention.
Figure 13:
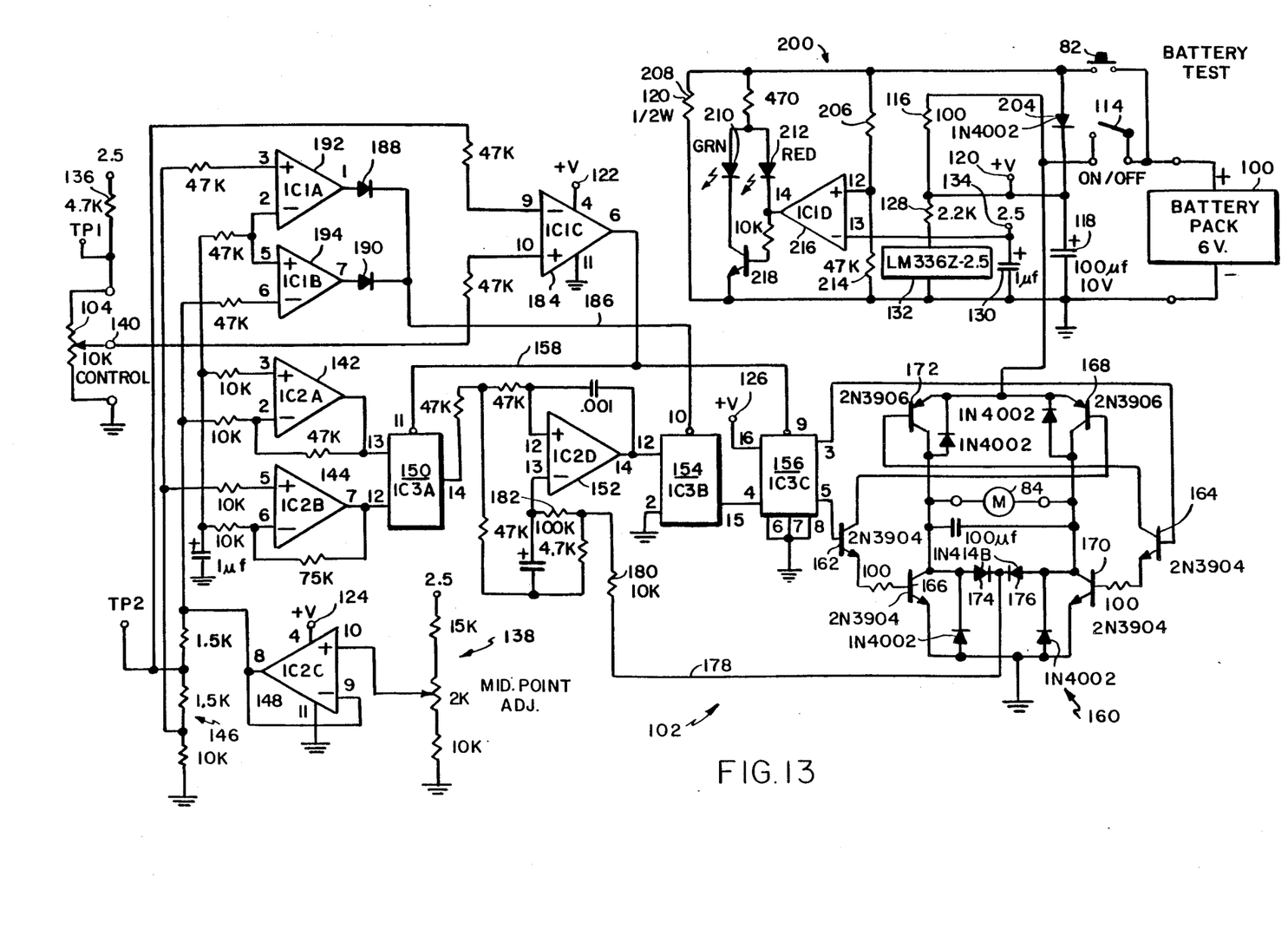
FIG. 13 is a schematic diagram of the control circuit for the operation of the ophthalmic aspirator-irrigator instrument according to the invention.
Figure 16:
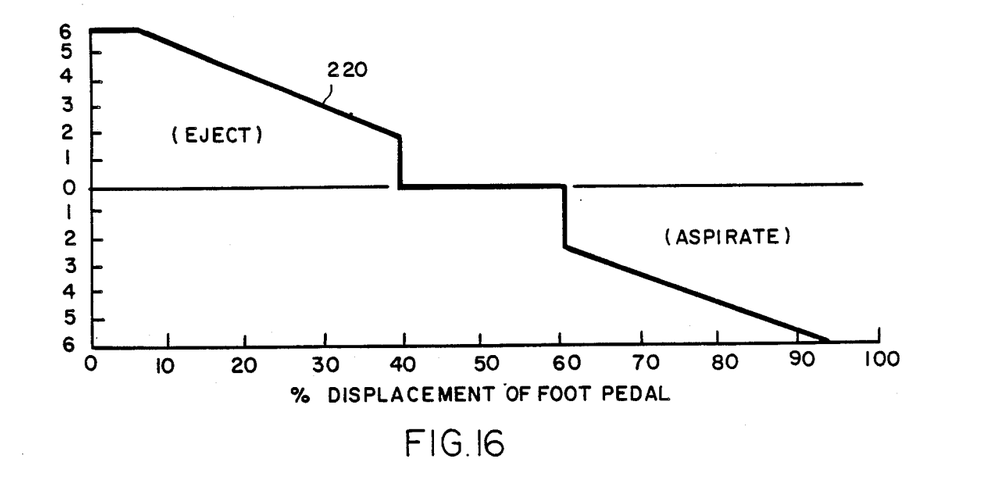
FIG. 16 is a graph useful in the understanding of the operation of the ophthalmic aspirator-irrigator instrument according to the invention.

The potentiometer's 104 electrical position, i.e., its wiper voltage, also is controlled by and is linearly proportional to the position of the foot pedal 24 along the pedal's arc of displacement 26. A layout of the control circuitry 102 is illustrated in FIG. 12 and a schematic of the circuitry 102 is shown in FIG. 13. The operative DC voltage applied to the DC motor 62 as a function of the pedal's 24 displacement from its shown, normally-off position in FIG. 2 and along the arc of displacement 26, is illustrated in FIG. 16.

As mentioned, the function of the circuitry 102 is to provide both speed and direction control, i.e., clockwise or counter-clockwise, to the DC motor 62, and that from a single control input, i.e., the foot pedal 24.

Operation of the Control Circuitry-FIGS. 12 and 13

Control circuitry 102 operates as follows. The power source 100 is connected to the circuitry 102 via a power micro-switch 114 integral with the potentiometer 104, observe FIG. 12. When the pedal 24 is in its shown horizontally rest position, (FIG. 2), the power switch 114 is off, hence no power is applied to the circuitry 102. When the pedal 24 is moved downward, (FIG. 16) power from the power source 100 is applied to the logic integrated circuits IC1, IC2, and IC3 via a filter circuit comprised of resistor 116 and capacitor 118. In FIG. 13, note the point +V marked 120, which is connected via leads, not shown to preserve clarity, to points also marked +V in the respective logic integrated circuits and identified by the reference characters 122, 124 and 126, respectively. Further filtering is provided by resistor 128 and capacitor 130 into a reference voltage regulator 132. The junction 134 of resistor 128 and capacitor 130, marked 2.5 within a circle, also is connected electrically to one end of a resistor 136, whose other end is connected to TP1, and also to a mid point adjuster circuit 138.

Wiper voltage from the potentiometer 104 is applied via lead 140 to the positive input of a positive amplifier 142, IC2A, and to the negative input of a negative amplifier 144, IC2B. The reference inputs to these amplifiers 142 and 144 are tied to a divider string 146 connected to the output of a voltage follower 148, IC2C, whose positive input is connected to the mid point adjuster circuit 138. The mid point adjuster circuit 138, together with the voltage follower 148 and the divider string 146, provide the proper offset voltages to the DC amplifiers 142 and 144 so that they will operate symmetrically about the center portion of travel of the pedal 24 along the arc 26. The outputs of the DC amplifiers 142 and 144 are respectively connected to the inputs of an electronic switch 150, IC3A, an analog multiplexer. A control voltage also is applied to the electronic switch 150 at pin 11. Depending on the level of this control voltage, the electronic switch 150 selects one of the inputs, either from amplifier 142 or 144, to be coupled to the positive input of a pulse-width modulated (PWM) gate circuit, IC2D. When a positive voltage is sensed at the input pin 12 of the PWM gate 152, its output at pin 14 will be high. This high output is then connected via another electronic switch 154, IC3B, to a direction control switch 156, IC3C. Direction control switch 156 determines whether the motor 84 is caused to rotate clockwise or counter-clockwise. Depending on the level of the control voltage at pin 9, which voltage is the same as applied to pin 11 of switch 150 via a lead 158, only one of the switch's 156 two outputs at pins 3 or 5 will be high at any one time. The outputs at pins 3 or 5 are coupled to a transistor bridge circuit 160.

A positive voltage appearing at the base of one of two input transistors 162 and 164 will cause its corresponding NPN transistor 166 and PNP transistor 168 if the former, and NPN transistor 170 and PNP transistor 172 if the latter, to saturate and apply motor voltage to the DC motor 84 in the proper polarity. One of two diodes 174 and 176 will sense this applied motor voltage, rectify it and direct it back via lead 178 and filter resistors 180 and 182 to the negative input at pin 13 of the PWM gate 152 as feed-back control. The feed-back control will shut down the outputs of the direction control switch 156 and consequently the applied motor voltage will also go to zero. This feedback process will repeat until the average feedback voltage equals the input control voltage at pin 9 of the switch 156. The duty cycle of the transistor bridge circuit 160 is thus changed and controlled by varying the DC input control voltage at pin 9 of the switch 156. Short width pulses are evident at slow motor speeds and longer pulses prevail at higher motor speeds. The DC motor 62 itself senses only a filtered DC voltage however and, being an inductive device, motor 62 provides a smooth, continuous rotational force to its drive shaft 88.

The control pins 9 of switch 156 and 11 of switch 150 are connected together via the lead 158 to the output at 8 of a comparator 184, IC1C. The positive input at 10 of the comparator 184 also is the wiper voltage generated by the potentiometer 104 and carried by lead 140. The negative input at 9 of the comparator 184 is referenced to a voltage at TP2, which is adjusted by the mid point adjuster circuit 138 to equal the wiper voltage at mid travel of the slide-type potentiometer 104. When the wiper voltage at the potentiometer 104 exceeds this mid travel voltage, the output of the comparator 184 at pin 8 will go high, causing thereby the switches 150 and 156 to change states and the direction of rotation of the DC motor 84 will reverse.

A control voltage also is applied to the electronic switch 154 at pin 10 thereof via lead 186. Lead 186 connects through diodes 188 and 190 to comparators 192 IC1A, and 194, IC1B, respectively. These comparators 192 and 194 are connected in a window detector configuration. The reference voltages into the comparators 192 and 194 at pins 3 and 6, respectively, are selected to be slightly above and slightly below the mid travel voltage. The wiper voltage at the potentiometer 104 also is applied via the lead 140 to the connected inputs of the comparators 192 and 194 at pins 2 and 5, respectively. When the wiper voltage is within the selected range, the control voltage applied to pin 10 of the electronic switch 154 will be low, causing thereby the switch 154 to connect to zero at pin 2 and assuring that the DC motor 62 will be off. The electronic switch 154 thus prevents search pulses from the PWM gate 152 during this selected window range and provides a motor-off state for the DC motor 62 when the foot pedal 24 is in the center of its downward travel along the arc 26 of its displacement.

A battery test circuit 200 also is connected to the power source 100 via a battery test button 82. When button 82 is depressed, power from the source 100 is applied to the test circuit 200 through a diode 204, to resistors 206 and 208, and to green and red LED's 210 and 212, respectively. Resistors 206 and 214 divide the battery source 100 voltage in half and apply it to the positive input at pin 12 of a comparator amplifier 216, IC1D. The negative input at pin 13 of the comparator amplifier 216 is tied to the reference voltage regulator 132, herein set at 2.500 volts. Consequently, if the battery source 100 voltage, herein set at 6 volts, drops below twice the 2.500 volts, i.e., below 5.000 volts, the output of the comparator amplifier 216 at pin 14 will go low, turning on the red LED 212. Otherwise, the comparator 216 output at pin 14 will remain high, providing base current into an NPN transistor 218 and turning the green LED 210 on. The resistor 208 simulates the drain of the DC motor 62 on the battery power source 100 during the test.

In FIG. 16 is illustrated a graph 220 plotting the DC voltage applied by the circuitry 102 of FIG. 13 to drive the micro DC motor 62 during the downward displacement of the foot pedal 24 along the arc 26, as against a percentage of displacement along this arc 26. With the pedal 24 slightly depressed, the power switch 114 is closed and full DC power, herein positive six volts, is applied to the DC motor 62 to drive it in full speed reverse, that is clockwise. As a consequence, the peristaltic pump 16 will rotate rapidly clockwise, creating a positive ejaculatory pressure through the aspiration port 52 of the central channel 50 of the cannula 14. As the pedal 24 progressively is more and more depressed, the applied voltage to the motor 62 will fall, decreasing thereby the rotational speed of the pump 16. With the gradual decrease of the pump's 16 speed, the magnitude of the positive ejaculatory pressure through the aspiration port 52 of the cannula 14 also becomes less and less. With about 40% downward displacement of the pedal 24 along the arc 26, a zero applied voltage to the motor 62 is achieved from a previous +2.1V, and the motor 62 and its drive shaft 17 will come to a full stop. As a result, the pump 16 also will cease rotating and no further ejaculatory pressure will be emanating from the port 52.

The zero applied voltage condition is maintained during a window through about 60% in the downward travel of the pedal 24 along the arc 26. Further downward motion of the pedal 24 first will apply a negative DC voltage slightly in excess of 2V to the motor 62, reversing its rotation into a counter-clockwise direction but with a slow initial speed. As a result, the pump 16 will begin slowly to rotate in a counter-clockwise direction, creating thereby a negative aspiratory pressure through the aspiration port 52 of the cannula 14. With the further gradual depression of the pedal 24, the negative applied voltage to the DC motor 62 also is increased, progressively increasing thereby the speed of rotation of the pump 16. Consequently, the negative aspiratory pressure through the aspiration port 52 also is increased. With about 90% in the extent of the downward travel of the pedal 24 along the arc 26, almost maximum -6 V is applied to the motor 62, bringing its rotational speed to the maximum. With the foot pedal 24 pressed all the way down (as shown in phantom lines in FIG. 2), maximum negative aspiration pressure is maintained through the aspiration port 52.

Preferably, the control circuitry 102 further incorporates a trigger circuit to trigger an audible signal producing means 222, note FIG. 10. Preferably, the trigger circuit is so designed as to produce one audible signal at the commencement of the aspiration through the aspiration port 52 and a second audible signal at the commencement of reflux (ejection) via the post 52 during the reverse motion of the front pedal 24 from the position shown in phantom lines to the rest position shown in solid lines in FIG. 2. Preferably, this signal producing means 222 is adjustable regarding the loudness of the signal emitted by it, as by the provision of a knob 224 designed for rotation about a limited arc of displacement.

Figures 3, 4, 5:
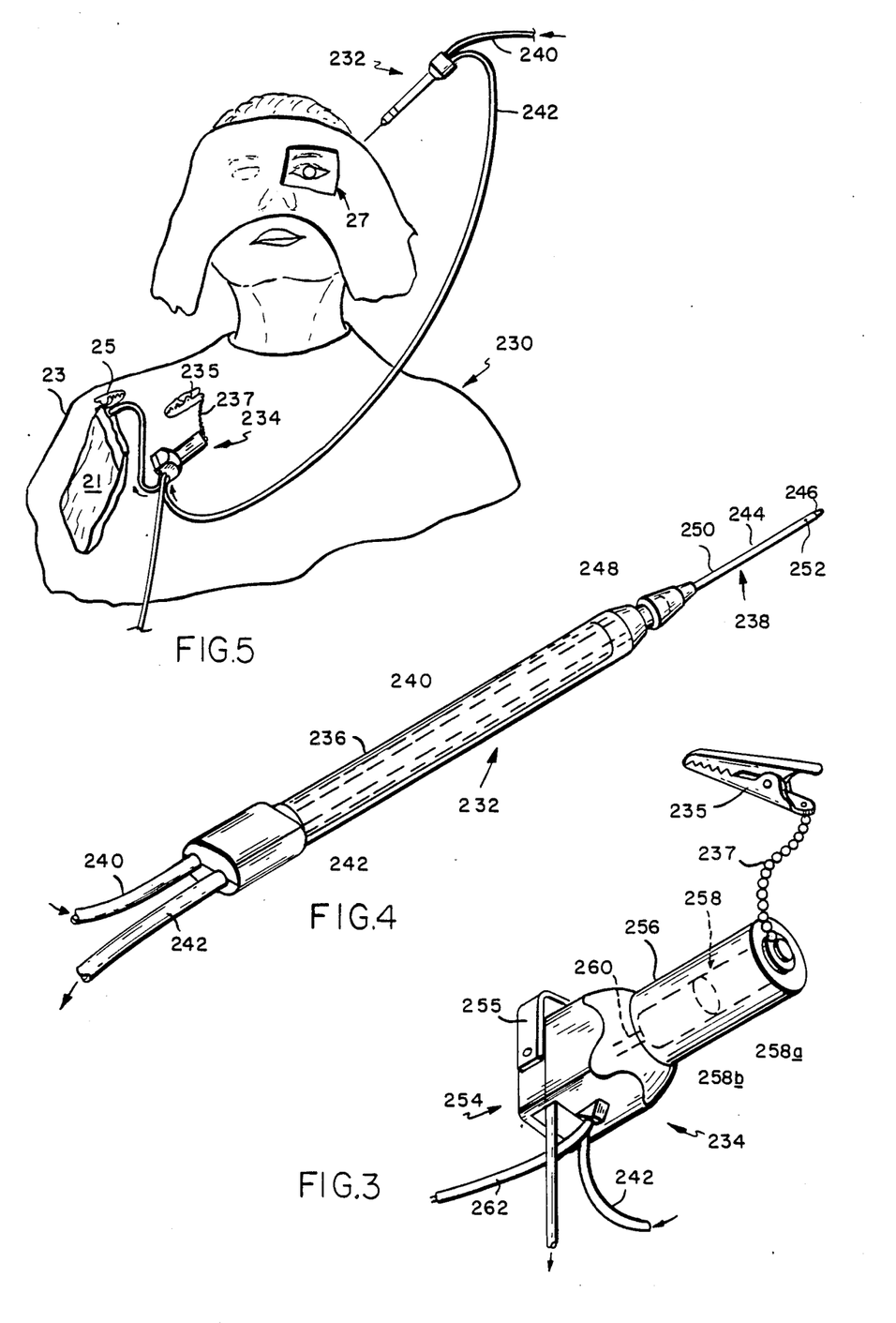
FIG. 3 is a perspective view of one part of a modified ophthalmic aspirator-irrigator instrument according to the invention.
FIG. 4 is a perspective view of another part of the modified ophthalmic aspirator-irrigator instrument.
FIG. 5 is a perspective view illustrating the operative use of the modified ophthalmic aspirator-irrigator instrument according to FIGS. 3 and 4.

The Embodiment of FIGS. 3, 4 and 5

A modified ophthalmic aspirator-irrigator instrument 230 is illustrated in FIGS. 3, 4 and 5. This modified instrument 230 essentially comprises a lighter hand-held piece 232 than the device 12, illustrated in FIG. 4, and a shortened drive section 234, illustrated in FIG. 3. However, the modified instrument 230 also is powered by and operated from the same control means 20 of FIG. 2 and with the aid of the same control circuitry 102 described with reference to FIGS. 12 and 13 above.

The light hand-held piece 232 of this modified instrument 230 comprises a hollow tubular housing 236, preferably formed of a rigid or semi-rigid plastic material, a cannula 238 and a pair of flexible tubes 240 and 242. The cannula 238 can be formed exactly the same as the cannula 14 shown in and described with reference to FIG. 1 above, and frictionally mounted to the frusto-conical front end of the piece 232. If so, the tube 240 would need to be connected thereto either just like the tube 32 in FIG. 1 or by having the tube's 240 end exit from the housing 236 at the front thereof so as to connect to the arm 58 of the cannula 14. In this event, the cannula 14 is preferably made of metal, such as stainless steel. The illustrated cannula 238 is, however, preferably formed with a hollow metal needle 244, provided with an aspiration port 246 in the front and with a connecting channel 248 in the rear, to which the end of the tube 240 is attached. A plastic sleeve member 250 is designed to surround the hollow metal needle 244 so as to form an annular channel about the axial length of the needle 244, in a fashion similar to that of the cannula 14, note especially FIG. 8. At its front end, the sleeve member 250 is provided with a pair of irrigation ports 252, whose orientation is similar to that of the ports 60 with respect to the port 52 of the cannula 14. The forward end of the tube 242 is in turn operatively connected to the annular channel formed between the needle 244 and the surrounding sleeve 250 so as to be in fluid communication therewith. Tube 240, just like the tube 32, also is connected to the saline containing bottle 30, via the clamp 36 and the filter 38, observe FIG. 6. Tube 242, on the other hand, is connected to the drive section 234, also shown secured to the surgical drape 23 adjacent the pouch 21 by means of a second clip 235. Preferably, a short chain 237 connects the clip 235 to one end of the drive section 234.

The drive section 234 is, for the most part, identical to the housing section 13, minus the forward conical part 15b, of the instrument 10 shown in FIG. 1. As best illustrated in FIG. 3, the drive section 234 also is provided with a pressure differential creating means 254, which is a peristaltic pump just like the pump 16, and held in place by a tube retaining member 255, just like the member 29. Inside a hollow housing 256, there is an identical drive means 258 comprising a D.C. micro motor 258a and a gear head 258b driving a shaft 260. The shaft 260 is drivingly coupled to the peristaltic pump 254. The tube 242, emanating from the hand-held piece 232, is trained about the peristaltic pump 254 and then is connected to the pouch 21, as illustrated in FIG. 5. A power cord 262 is, in turn, connected to the footpedal control means 20, shown in and described with reference to FIG. 2.

Figures 14, 18:
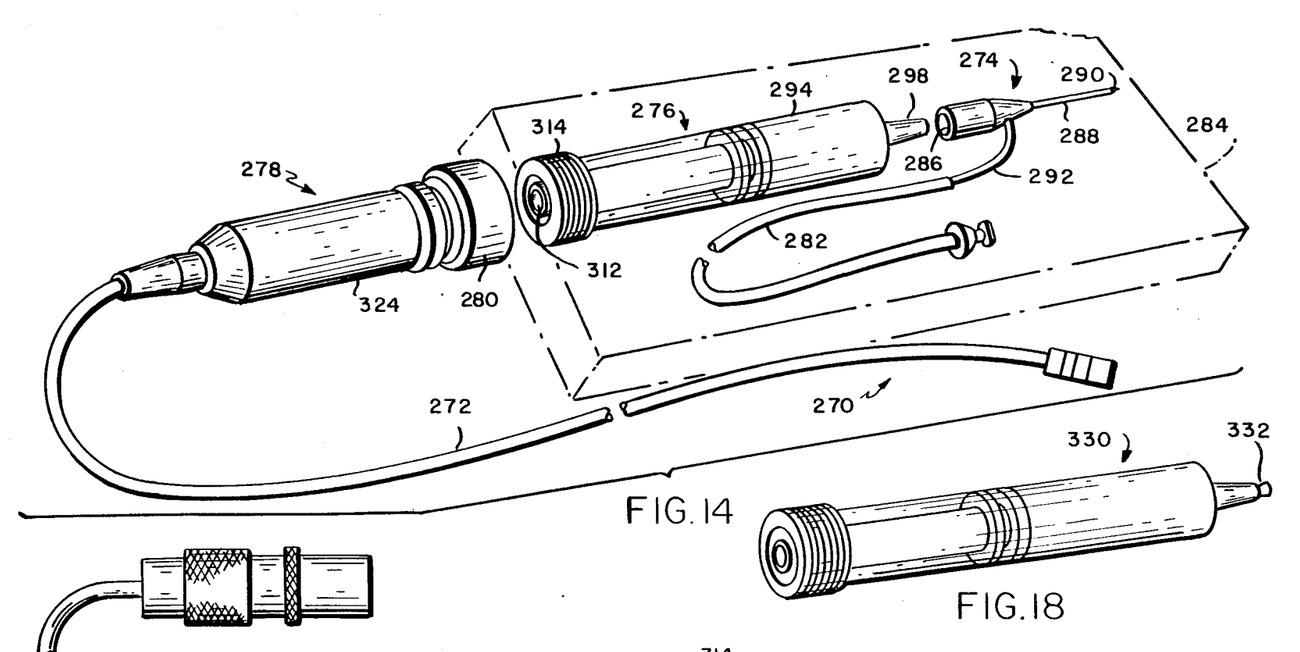
FIG. 14 is a perspective explosive view of another embodiment of an ophthalmic aspirator-irrigator instrument constructed in accordance with the present invention.
FIG. 18 is a perspective view of a revised component part of the ophthalmic aspirator-irragator instrument illustrated in FIGS. 14 and 15.
Figure 15:
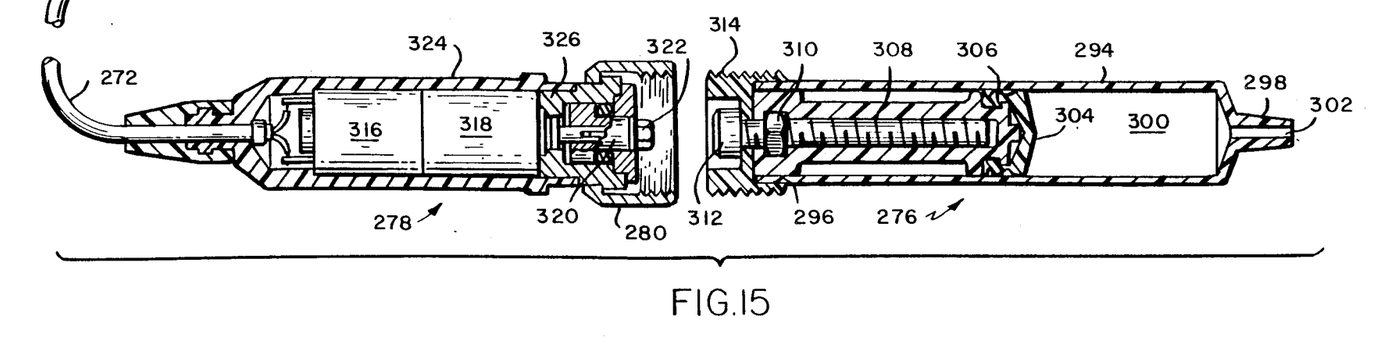
FIG. 15 is a longitudinal section, partly in elevation, of a portion of the ophthalmic aspirator-irrigator instrument of FIG. 14.

The Embodiments of FIGS. 14, 15 and 18

In FIGS. 14 and 15, another preferred embodiment of an ophthalmic aspirator-irrigator instrument 270 constructed in accordance with the present invention is illustrated. The ophthalmic aspirator-irrigator instrument 270 also comprises a hand-held device, with a flexible power cord 272 coupling it to the control means 20 of FIG. 2. The hand-held instrument 272 also includes a cannula 274, a pressure-differential creating means 276 designed frictionally to engage and hold the cannula 274, and drive means 278 releasably connected to the pressure-differential creating means 276 by means of a ring 280. The source of fluid 30, illustrated in FIG. 6 and containing a saline solution, is connected via a flexible tube 282 to the cannula 274. The bottle 30 again allows for the gravity-feeding of the fluid via the cannula 274 into the eye. The clamp 36 and the appropriate filter 38 preferably also are incorporated in the tube 282. Preferably, both the cannula 274 and the pressure-differential creating means 276 are enclosed in a container 284 to maintain the same in sterile condition. Following use, both the cannula 274 and the pressure-differential creating means 276 preferably are discarded. On the other hand, the drive means 278 and the thereto attached power cord 272, which are autoclavable, preferably are sterilized before use. Sterilization may be effected in an autoclave, by gamma sterilization or by ETO.

It is to be again noted that cord 272 is but a power cord, carrying but an electrical signal. It is not a long tubing connecting the cannula 274 to a pump for creating the required negative aspiration pressures, as in some prior art devices, which can cause fluctuations in the aspiration pressures and delays in the use of the instrument.

The cannula 274 is just like the cannula 14 and comprises two parts: a hollow cone 286 and a needle 288 concentrically extending therefrom. The needle 288 is formed with a central channel which is in fluid communication with the hollow cone 286 at one end, and terminates in an aspiration port 290 located in the front tapered portion of the needle 288. An annular channel surrounds the central channel and is in fluid communication with a hollow arm 292 at one end, and terminating in a pair of irrigation channels also formed in the tapered portion of the needle 288 but offset from the aspiration port 290 and at right angles thereto, similar to the one shown in FIG. 8. The hollow arm 292 preferably is formed integral with the hollow cone 286 of the cannula 274, as by injection forming or compression molding a suitable plastic material, such as polypropylene, in a suitable mold (not shown) in which the needle 288 had been inserted previously. The needle 288 however preferably is made of metal, such as stainless steel. Of course, if desired, the entire cannula 274 also can be formed from metal.

The pressure-differential creating means 276, whose function is to create a pressure-differential within the central channel of the cannula 274, also is preferably formed of a suitable plastic material, such as polypropylene or the like, as by injection forming or compression molding in a suitable mold, not shown. The pressure-differential created by the means 276 also is with respect to ambient, and can be either a positive or a negative pressure emanating from the aspiration port 290 depending on how it is driven by the drive means 278. The pressure-differential creating means 276 essentially is formed like a syringe, having a tubular body 294 open at one end 296 and ending in a frusto-conical shape 298 at the other end. This frusto-conical shape 289 is designed to be frictionally engaged by the hollow cone 286 of the cannula 274 when the same is releasably secured thereto immediately prior to the instrument's 270 operative use during cataract surgery.

With the hollow cone 286 of the cannula 274 in place over the frusto-conical shaped end 298 of the pressure-differential creating means 276, the central channel of the cannula 274 is in fluid-communication with an inner chamber 300 formed within the tubular body 294 via a channel 302, all as may be best observed in FIG. 15. A plunger 304 is designed to be axially displaced within the chamber 300. The plunger 304 is formed with an axial channel 306 to accommodate an externally threaded drive shaft 308 designed to rotate, and thus be axially displaced, within a hexagonal standoff 310 secured in the rear end of the plunger 304. A hexagonal socket 312 is formed in the free end of the drive shaft 308. Rotating the drive shaft 308 clockwise will cause the plunger 304 to travel toward the rear (to the left in FIG. 15) within the tubular body 294. An externally-threaded sleeve 314 is secured about the rear end 296 of the tubular body 294 to prevent the plunger 304 from being withdrawn therefrom, the condition shown in FIG. 15. A counter-clockwise rotation of the drive shaft 308 will now cause the plunger 304 to travel forward (i.e., to the right in FIG. 15 ) within the inner chamber 300 until the plunger 304 abuts the front end of the tubular body 294.

When the plunger 304 travels forward, it creates a positive pressure within the central channel of the cannula 274, causing whatever may be within the chamber 300, the channel 302, the control channel or the aspiration port 290 (be it air, liquid or slurry) to be ejected therefrom via the aspiration port 290. Conversely, when the plunger 304 is caused to travel backward, it creates a negative pressure within the central channel of the cannula 274, causing the cannula 274 to aspirate via the aspiration port 290 whatever may be in the vicinity of the aspiration port 290.

The drive means 278 for driving the pressure-differential creating means 276 also is similar to the drive means 18 in FIG. 1 and essentially comprises a DC micro-motor 316, a gear head 318, and a drive shaft 320. Shaft 320 is provided with a hexagonal head 322 designed to fit within and mate with the hexagonal socket 312 of the drive shaft 308. The motor 316 and its gear head 318 preferably are mounted within a suitable plastic tubular housing 324. The connecting ring 280, which is internally-threaded, is rotatably secured about a shoulder of a motor-mount 326 and is designed to mate with and to be secured about the sleeve 314, releasably securing thereby the drive means 278 to the pressure-differential creating means 276. Preferably, the ring 280 is formed of a light metal, such as aluminum.

In FIG. 18, there is illustrated a revised component part 330 for use in the ophthalmic aspirator-irrigator instrument 270 shown in and described with reference to FIGS. 14 and 15. With the aid of this revised component part 330, the instrument 270 also is useful in an alternative manner for a different kind of operation. This alternative use involves the controlled injection of a viscous material into various parts of the human or animal body.

As will be noted, part 330 takes the place of the pressure-differential creating means 276, i.e., the pump. Its forward end of the part 330 preferably is a bit longer than that of the part 276, which makes the inner chamber of the part 330 correspndingly longer than is the chamber 300 of the part 276. This enlarged chamber of the revised part 330 is preloaded with the viscous material. The viscous material is maintained in an air tight environment between the plunger 304, which of course remains the same, and a plug 332 designed temporarily to block the channel 302. The plug 332 is then broken off by the user before the part 330 is inserted into the cannula 274 immediately prior to its operative use. The plug 332 may be formed integral with the body of the part 330 or it may be inserted into the channel 302 after its inner chamber has been filled with the viscous material.

The viscous material may, of course, comprise any suitable material intended to be injected into the various parts of the body and its selection will be dictated by the end use thereof. One such viscous material comprises a paste made of teflon and glycerine, which paste is useful, inter alia, to reorient defective vocal cords or to relieve urinary incontinence by injection thereof adjacent to the ureter to build resistance to uncontrolled urine flow. Other uses will readily suggest themselves to those skilled in the art.

The preloaded revised component part 330 also is mated to the same drive means 278 above described. This time, however, the plunger 304 will be caused to travel in the forward direction only by the counter-clockwise rotation of the drive shaft 308 by the use of the variable speed reflex mode of the foot operated control unit 20. The surgeon-operator thus has precise control of the speed and the amount of the viscous material that is injected by the revised instrument into the various parts of the human body. Following use, the revised component part 330 is conveniently discarded, even in instances when only a portion of the preloaded viscous material therein has been used up.

Thus it has been shown and described an ophthalmic aspirator-irrigator instrument designed for use during cataract surgery, which instrument satisfies the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. An ophthalmic aspirator-irrigator comprising:
   (a) a hand-held device;
   (b) said device including a cannula having an axial channel and a surrounding annular channel, pressure-differential creating means connected to said axial channel, and drive means operatively connected to said last means for driving the same;
   (c) a source of fluid connected via a flexible tube to said annular channel;
   (d) foot-operable control means for controlling the operation of said drive means and provided with a pedal, a power source, a circuit connected to said source, and a socket coupled to said circuit;
   (e) a flexible power cord having a plug designed to be connected to said socket for coupling power from said power source to said drive means; and
   (f) a container enclosing said cannula and said pressure-differential creating means;
   (g) said foot-operable control means being portable and said power source comprising a battery pack.

2. The ophthalmic aspirator-irrigator of claim 1 wherein said cannula is provided with a tapered tip, an aspiration port formed in the side of said tapered tip and connecting with said axial channel and at least one irrigation opening also formed in the side of said tapered tip and at a right angle thereto and connecting with said surrounding annular channel.

3. The ophthalmic aspirator-irrigator of claim 1 wherein said pressure differential creating means includes a D.C. micro-motor, a gear head connected to said motor, a peristaltic pump and a shaft coupling said motor via said gear head to said pump 4. The ophthalmic aspirator-irrigator of claim 1 wherein said circuit includes dual D.C. amplifiers and a pulse-width modulated gate circuit and wherein said circuit controls said drive means bidirectionally with a smooth, continuous speed control effected by an electrical signal generated by said dual D.C. amplifiers, said signal coupled to said pulse-width modulated gate circuit.

5. The ophthalmic aspirator-irrigator of claim 4 further including an audio signal generating means.

6. The ophthalmic aspirator-irrigator of claim 5 wherein said circuit includes a linear motion slide-type potentiometer controlled by said pedal.

7. The ophthalmic aspirator-irrigator of claim 1 wherein said pressure-differential creating means is provided with an externally-threaded sleeve and said drive means is provided with an internally-threaded connecting ring, whereby said drive means is releasably connected to said pressure-differential creating means.

8. An ophthalmic aspirator-irrigator comprising:
   (a) a hand-held device;
   (b) a pressure-differential creating means coupled via a flexible tube to said device;
   (c) a foot-operable control box;
   (d) a power cord for operatively connecting said control box to said pressure differential creating means;
   (e) a collection pouch coupled to said pressure-differential creating means for collecting material aspirated by said device;
   (f) a source of fluid connected via a flexible tube to said hand-held device; and
   (g) fastening means respectively provided for said pressure-differential creating means and said collection pouch, to secure them respectively adjacent a surgical site;
   (h) said foot-operable control box provided with a pedal and including a power source and a circuit.

9. The ophthalmic aspirator-irrigator of claim 8 further including an audio signal generating means.

10. The ophthalmic aspirator-irrigator of claim 9 wherein said single control unit comprises a linear motion slide-type potentiometer controlled by said pedal and wherein said circuit comprises dual DC amplifiers coupled to said potentiometer, electronic switch means connected to the outputs of said DC amplifiers, and a pulse-width modulated gate circuit coupled to said drive means and via said electronic switch means to one of the outputs of said DC amplifiers, whereby the position of said foot pedal along its arc of displacement controls both the speed and the direction of said drive means and the operation of said audio signal generating means.

11. The ophthalmic aspirator-irrigator of claim 10 wherein said circuit further includes a comparator network to disable said switch means between the output of said pulse-width modulated gate circuit and said bridge circuit when said foot pedal is located about midway along said arc of displacement.

12. An ophthalmic aspirator-irrigator comprising:
   (a) a hand-held device including a cannula, a pressure-differential creating means connected to said cannula, drive means for bidirectionally driving said pressure-differential creating means, and connecting means for releasably securing said cannula to said pressure-differential creating means;
   (b) a portable control box for controlling both the speed and the direction of said drive means and provided with a foot pedal having an arc of displacement, a power source, and a circuit coupled via a switch to said foot pedal and said power source;
   (c) a flexible power cord connecting said power source to said drive means;
   (d) said circuit including a linear motion slide type potentiometer operatively connected to said foot pedal and generating a voltage linearly proportional to the position of said pedal along its said arc of displacement, dual DC amplifiers coupled to said potentiometer to receive said voltage at one of their inputs, a reference voltage connected to the other inputs of said amplifiers, switch means coupled to the outputs of said amplifiers, a pulse-width modulated gate circuit coupled to the output of said switch means, a bridge circuit operatively connected via said flexible power cord to said drive means, and a direction control switch coupling the output of said pulse-width modulated gate circuit to said bridge circuit.

13. The ophthalmic aspirator-irrigator of claim 12 wherein said cannula is formed with an axial channel and a surrounding annular channel and further including a source of gravity-fed fluid connected via a flexible tube to said surrounding annular channel of said cannula, and further including a plastic container for maintaining said cannula and said pressure-differential creating means in a sterile condition.

14. The ophthalmic aspirator-irrigator of claim 13 wherein said cannula is formed with a tapered tip, an aspiration port formed in said tapered tip and being in communication with said axial channel, and a pair of irrigation openings formed in said tapered tip adjacent to but at right angles to said aspiration port and being in communication with said annular channel.

15. The ophthalmic aspirator-irrigator of claim 12 wherein said circuit further includes a comparator network to disable said switch means between the output of said pulse width modulated gate circuit and said bridge curcuit when said foot pedal is located about midway along said arc of displacement.

16. An ophthalmic aspirator-irrigator comprising:
(a) a hand-held device;
(b) said device including a cannula formed with a hollow cone and a concentric needle, said needle having a central channel in communication with said hollow cone at one end and terminating in a port at the other end and an annular channel surrounding said central channel and terminating in a pair of irrigation openings at its free end;
(c) a pressure-differential creating means operatively connected to said hollow cone and drive means for said pressure-differential creating means mounted adjacent thereto;
(d) a foot operable control box including a source of power;
(e) a power cord for operatively connecting said pressure differential creating means to said control box; and
(f) a source of fluid connected via a flexible tube to said annular channel of said cannula;
(g) said foot-operable control box provided with a foot pedal, a jack for said power cord, visible and manually operable test means for said source of power, an audio signal generating means, means for varying the intensity of said audio signal, and further including a power source and a circuit.

17. The ophthalmic aspirator-irrigator of claim 16 wherein said circuit provides said drive means bidirectionally with a smooth, continuous and variable speed control, said circuit controlling both the speed and the direction of said drive means and the operation of said audio signal generating means via a single control unit, and wherein said single control unit comprises a linear motion slide-type potentiometer controlled by said pedal.

18. The ophthalmic aspirator-irrigator of claim 16 further including a plastic container for maintaining said cannula and said pressure-differential creating means in a sterile condition.

* * * * *